(12) United States Patent
Catalfo et al.

(10) Patent No.: US 6,596,266 B2
(45) Date of Patent: Jul. 22, 2003

(54) COMPOSITIONS CONTAINING MINOXIDIL AND SAW PALMETTO FOR TREATING BALDNESS

(75) Inventors: Chris Catalfo, Orlando, FL (US); Fred Mussari, Melbourne, FL (US); Stephen H. Perry, Longwood, FL (US)

(73) Assignee: Natural Science, Inc., Melbourne, FL (US)

( * ) Notice: Subject to any disclaimer, the term of this patent is extended or adjusted under 35 U.S.C. 154(b) by 0 days.

(21) Appl. No.: 09/789,294

(22) Filed: Feb. 20, 2001

(65) Prior Publication Data

US 2002/0028257 A1 Mar. 7, 2002

Related U.S. Application Data

(60) Provisional application No. 60/183,553, filed on Feb. 18, 2000.

(51) Int. Cl.$^7$ .............................. A61K 7/06; A61K 35/78
(52) U.S. Cl. ..................... 424/74; 424/70.1; 424/725; 424/727
(58) Field of Search ................................ 424/750, 70.1, 424/195.17, 74, 725, 727; 435/975

(56) References Cited

U.S. PATENT DOCUMENTS

| | | | |
|---|---|---|---|
| 3,551,554 A | 12/1970 | Herschler | |
| 3,989,816 A | 11/1976 | Rajadhyaksha | |
| 4,017,641 A | 4/1977 | DiGiulio | |
| 4,082,881 A | 4/1978 | Chen et al. | |
| 4,132,781 A | 1/1979 | Stoughton | |
| 4,139,619 A | 2/1979 | Chidsey, III | |
| 4,485,054 A | 11/1984 | Mezei et al. | |
| 4,596,812 A | 6/1986 | Chidsey, III et al. | |
| 4,761,288 A | 8/1988 | Mezei | |
| 4,828,837 A | 5/1989 | Uster et al. | |
| 4,861,764 A | 8/1989 | Samour et al. | |
| 5,026,691 A | 6/1991 | Kligman | |
| 5,030,442 A | 7/1991 | Uster et al. | |
| 5,183,817 A | 2/1993 | Bazzano | |
| 5,407,944 A | 4/1995 | Goldman | |
| 5,466,695 A | 11/1995 | Poulos et al. | |
| 5,578,599 A | 11/1996 | Diani et al. | |
| 5,609,858 A | 3/1997 | Buck | |
| 5,618,798 A | 4/1997 | Bar-Shalom | |
| 5,620,980 A | 4/1997 | Samour | |
| 5,656,300 A | 8/1997 | Levin | |
| 5,720,946 A | 2/1998 | Takeda et al. | |
| 5,750,107 A | 5/1998 | Nomura | |
| 5,750,108 A | 5/1998 | Edwards | |
| 5,763,361 A | 6/1998 | Harris et al. | |
| 5,834,014 A | 11/1998 | Weiner et al. | |
| 5,925,679 A | 7/1999 | Mather et al. | |
| 6,284,234 B1 * | 9/2001 | Niemiec et al. | .......... 424/78.07 |
| 2001/0031286 A1 * | 10/2001 | Porras et al. | .............. 424/750 |

FOREIGN PATENT DOCUMENTS

| | | |
|---|---|---|
| EP | 0728462 A2 | 8/1996 |
| JP | 05286835 | 2/1993 |
| WO | WO 92/16236 | 10/1992 |
| WO | WO 94/17776 | 8/1994 |
| WO | WO 95/00495 | 1/1995 |
| WO | WO 95/25500 | 9/1995 |
| WO | WO 97/03638 | 2/1997 |
| WO | WO 97/12602 | 4/1997 |
| WO | WO 97/15558 | 5/1997 |
| WO | WO 97/38728 | 10/1997 |
| WO | WO 97/47276 | 12/1997 |

OTHER PUBLICATIONS

Barry, B.W. and Bennett, S.L., "Effect of penetration enhancers on the permeation of mannitol, hydrocortisone and progesterone through human skin", *J. Pharm. Pharmacol.*, 1987, 535–546: 39.

Brodland, D.G. and Muller, S.A., "Androgenetic Alopecia (Common Baldness)", Cutis, 1991, 173–176:47.

Katz, H. I., "Topical Minoxidil: Review of Efficacy", *Clinics in Dermatology*, 1998, 195–199: 6.

Prager, N. et al., "A Randomized, Double–Blind, Placebo–Controlled Trial to Determine the Effectiveness of Botanically Derived Inhibitors of a 5–α–Reductase in the Treatment of Androgenetic Alopecia", *The Journal of alternative and Complementary Medidicine*, 2002, 143–152:8.

Puolakka, Jukka, "Serum Ferritin in the Evaluation of Iron Status in Young Healthy Women", Acta *Obstet Gynecl Scand Suppl.*, 1980, 35–41:95.

Rushton, D. H. and Ramsay, I. D., "The imprtance of adequate serum ferritin levels during oral cyproterone acetete ethinyl oestradiol treatment of diffuse androgen–dependent alopecia in women", *Clinical Endocrinology*, 1992, 421–427:36.

Sattar, A.B. et al., "Chemical composition and biological activity of leaf exudates from some Lamiaceae plants", *Pharmazie*, 1995, 62–65:50.

\* cited by examiner

Primary Examiner—David M. Naff
Assistant Examiner—Deborah K. Ware
(74) Attorney, Agent, or Firm—Van Dyke & Associates, P.A.

(57) ABSTRACT

Compositions and/or formulations containing minoxidil as an active ingredient in combination with other active agents and/or enhancer agents (e.g., saw palmetto extract and nettle root extract) are provided. The compositions and/or formulations increase the hair growth capability of the composition. Also disclosed are methods of using the compositions to treat male patterned baldness and to stimulate hair growth on the scalp, including both the apex and frontal regions of the scalp.

16 Claims, No Drawings

COMPOSITIONS CONTAINING MINOXIDIL AND SAW PALMETTO FOR TREATING BALDNESS

CROSS-REFERENCE TO RELATED APPLICATIONS

The subject application claims the benefit under 35 USC §119(e) of Provisional Application No. 60/183553 filed Feb. 18, 2000.

BACKGROUND OF THE INVENTION

Androgenic alopecia is the single largest type of recognizable alopecia to affect both men (50%) and women (30%), primarily of Caucasian origin. Androgenic alopecia or common baldness represents 99 percent of all cases of hair loss (Brodland and Muller, 1991). The condition is characterized by the gradual conversion of terminal hair to short, wispy, colorless vellus hair.

It is generally accepted that genetic hair loss arises from an inherited predisposition activated by circulating androgenic hormones. While many investigators have tried to isolate the causative androgen metabolite, no single molecule has emerged. For example, in comparative studies between non-balding controls, no significant difference between mean hormonal values or amounts has been detected. See Puolakka, 1980. This suggests that a sensitivity or receptivity to hormones at the cell binding sites within the dermal papilla is a possible factor. Several treatments are based on this theory using anti-androgens such as CPA (cyproterone acetate) in combination with ethinyl-estradiol and the aldosterone antagonist spironolactone, which, given in dosages from 75 to 100 mg per day has shown some benefit. See e.g., Rushton and Ramsay, 1992; Rushton et al. 1991.

Most treatment modalities currently employed (such as hair transplantation) have been performed based on the theory that some hair follicles are genetically predisposed for sensitivity to androgens in the body. However, transplantation methods can be painful and expensive, often resulting in an undesirable "fake" appearance. No single treatment modality has proven completely or repeatably successful in inducing, maintaining and/or increasing hair growth.

In 1980, the reversal of androgenic alopecia in a male patient receiving minoxidil for hypertension was revealed and minoxidil has since been used to promote hair growth, most commonly by topical application (Zapacosta, 1980). Minoxidil's vasodilating effect on the scalp is one of the proposed mechanisms by which minoxidil promotes hair growth. However, despite its popularity, minoxidil has not performed in a completely satisfactory fashion in promoting hair growth in all target populations. While minoxidil has been shown to stimulate some hair growth at the apex region of the scalp, hair growth at the frontal region of the scalp, for the most part, has not been shown to be improved by minoxidil treatment alone.

Cosmetic treatment of age-related hair loss in androgenic alopecia patients with topical solutions of minoxidil (ROGAINE®) alone, or in combination with skin penetration enhancers, such as DMSO, has resulted in only moderate regrowth of hair in less than 40% of such patients (Katz, 1988). Moreover, treatments with topical solutions of minoxidil require multiple applications of the active ingredient each day, which can be very inconvenient as well as expensive.

There is a need for methods of treating hair loss that require fewer applications of active ingredient, e.g., minoxidil, and which will also provide hair regrowth sooner, in more abundance, and thicker, than is presently observed using minoxidil and known penetration enhancers. Further, there is a need for a hair loss treatment which can improve hair growth at the frontal as well as apex regions of the scalp.

BRIEF SUMMARY OF THE INVENTION

The subject invention pertains to novel compositions and/or formulations containing minoxidil as an active ingredient in combination with other active agents and/or enhancer agents which increases the hair growth capability of the composition. Another aspect of the subject invention pertains to methods of using the novel compositions to treat male patterned baldness and to stimulate hair growth on the scalp, including both the apex and frontal regions of the scalp. In addition to, or in place of minoxidil, glycerol oxido esters and/or ketoconazole can be added to the subject hair growth compositions.

According to one aspect, the subject invention pertains to a topical composition designed for application to the scalp wherein said composition comprises, in admixture with a pharmaceutically acceptable carrier and minoxidil, one or more of the following components: saw palmetto extract; nettle root extract; Capsaicin; Niacin; Gingko Biloba; horsetail extract; phospolipid; glycero oxido esters; ursolic acid; ketoconazole; 1,4:3,6 dianhydro-2.5-di-o-methyl-D-glucitol; cycoldextrin; peppermint oil; or milk thistle. A particular aspect of the subject invention pertains to a composition for treating androgenic alopecia comprising minoxidil in combination with saw palmetto extract. A further aspect of the subject invention preferably comprises, in addition to the minoxidil and saw palmetto extract, a nettle root extract.

The subject compositions and methods provide a safe and effective way to increase hair growth of the scalp. These and other advantageous aspects of the subject invention are described in further detail below.

DETAILED DISCLOSURE OF THE PREFERRED EMBODIMENTS

The subject invention is directed to novel compositions and methods of using the same for treating androgenic alopecia, or male pattern baldness. The subject compositions comprise minoxidil as one active component in combination with other compounds which act in combination with minoxidil to synergistically increase the effectiveness of the composition. As used herein "minoxidil" refers to 2,4, pyrimidihediamine6-(1-piperdinyl)-3-oxide, and analogs and salts thereof, as described in U.S. Pat. Nos. 4,139,619; 4,596,812; and 5,030,442 which are incorporated herein by this reference. Alternatively, glycerol oxido esters, ketoconazole, or a combination thereof can be substituted for minoxidil, or otherwise added to the subject compositions in addition to minoxidil.

One embodiment of the subject invention is directed to a composition comprising minoxidil and saw palmetto extract in combination with at least one other inert compound whereby said composition is in a pharmaceutically-acceptable form suitable for topical administration. Conventional pharmaceutical forms for this purpose include ointments, waxes, gels, lotions, pastes, jellies, sprays, aerosols, and the like in aqueous or nonaqueous formulations. The term "ointment" embraces formulations (including creams) having oleaginous, absorption, water-soluble and emulsion-type bases, e.g., petrolatum, lanolin, polyethylene glycols, N-methyl-2-pyrrolidinone, oleyl alcohol as well as mixtures of these. In an alternative embodiment, the subject invention is directed to a composition comprising minoxidil in combination with a nettle root extract.

Some evidence suggests that saw palmetto extract can act as a DHT inhibitor. The term "DHT inhibitor" is used herein in its broad sense and relates to substances that inhibit enzymes responsible for producing dihydrotestosterone, such as 5-α-reductase, or otherwise block or mask activity of DHT by binding to DHT thereby inactivating it and/or binding to DHT receptors. In addition to, or in place of saw palmetto extract, other DHT inhibitors can be provided in the subject compositions, including, but not limited to, nettle root extract, azelaic acid (see e.g., U.S. Pat. No. 5,925,679), and ginko biloba.

In a more preferred embodiment, the subject composition comprises minoxidil, saw palmetto extract, and nettle root extract, wherein the composition comprises about 1% to about 5% minoxidil, about 3% to about 8% saw palmetto extract, and about 1% to about 3% nettle root extract.

Diffusional resistance of the stratum corneum to topically applied agents has been demonstrated with various drugs. In order to overcome this barrier effect a number of compounds can be added to the subject compositions to enhance the transdermal delivery of drugs, such as dimethyl sulfoxide (DMSO); polyethylene glycol monolaurate; alkyl lactams; long chain amides, substituted 1,3-dioxacyclopentanes and substituted 1,3-dioxacyclohexanes; 1,4:3,6 dianhydro-2.5-di-o-methyl-D-glucitol; or mixtures thereof. For example, U.S. Pat. No. 3,551,554 discloses DMSO, U.S. Pat. No. 3,989,816 discloses 1-substituted azacycloheptane-2-one, U.S. Pat. No. 4,132,781 discloses a topical antibiotic composition containing 2-pyrrolidone or an n-lower alkyl-2-pyrrolidone, U.S. Pat. No. 4,017,641 discloses propylene glycol and 2-pyrrolidone-containing compositions and U.S. Pat. No. 4,861,764 discloses 1,3-dioxolane and 1,3-dioxane derivatives as percutaneous absorption enhancers, U.S. Pat. No. 4,082,881 discloses 1,4,3,6 dianhydro-2,5,-di-o-methyl-D-glucitol (see also Barry, *Pharm. Pharmocol.*, 39:535–546 (1987)). WO 92/16236 discloses methods and compositions for enhancing the rate of absorption of topically administered physiologically active compounds. Minoxidil is disclosed as one of these compounds. Also, the penetration enhancers can be amino alcohol derivatives which may form a 1,3-dioxane ring.

Another example of an enhancing agent is 1,3-dioxacycloalkane taught, for example, in U.S. Pat. No. 5,620,980 whose teachings are incorporated herein by reference. Other agents include retin A or derivatives thereof such as tretinoin.

Other compounds which work to increase circulation to the cells of the scalp may be added to the subject compositions. These compounds are believed to not only increase health of the cutaneous and subcutaneous tissue of the scalp, but to aid in the delivery and penetration of active components as well. Compounds aiding in circulation which may be used in accord with the teachings herein include, but are not limited to, thistle, Ginkgo Biloba, and peppers (e.g., Cayenne pepper and Red pepper), ursolic acid (disclosed in Jap. Pat. No. 05286835, and Sattar et al., Pharmazie, 50:62–65 (1995)), or combinations thereof.

Some have hypothesized that there is a chronic inflammatory process, subtending to the hair bulbs, in patterned alopecia, leading to eventual scarring of the lower follicle, making regrowth impossible. To counter this inflammatory degenerative process, anti-inflammatories may also be added to the subject compositions. Such anti-inflammatories include steroidal as well as non-steroidal anti-inflammatories. Examples of anti-inflammatory agents useful in accord with the teachings herein include corticosteroids, ibuprofen and derivatives thereof, aspirin and derivatives thereof, aloe vera, and combinations thereof. The concentrations of steroidal compounds are preferably 0.5% to 2.5% of the subject composition. The concentration of non-steroidal compounds is preferably from about 1% to about 5%.

Antimicrobials may also be added to the subject compositions for treating alopecia. Examples of antimicrobials include, but are not limited to, organic solvents (e.g., alcohols) and oils or extracts (e.g., oil of wintergreen and peppermint oil), ursolic acid, or combinations thereof.

Compounds to aid in repair of hair, nails, and skin may also be added to the subject compositions. Examples of such compounds include selenium and silica, which may be added in relatively isolated form or in the form of various partially processed plant material or extracts (e.g., Horsetail-plantain or nettle root extract).

In a topical application, the compound or formulated composition can be applied to the area to be treated, in mammals such as the scalp in humans, by spraying, dabbing or swabbing. Other less specific methods can be employed provided the active ingredient(s) are delivered to the region of a hair follicle. Preferably, the compound or formulated composition is periodically applied to the treatment area on a routine basis prior to, during and subsequent to hair growth. Generally, the routine treatment would be to apply the compound or formulated composition at least daily, preferably twice daily although more frequent applications can be used. The percentage by weight of the active ingredients minoxidil or other vasodilator herein utilized range at an effective amount which is an amount sufficient to increase normal hair growth or treat various forms of alopecia whereby the hair growth is significantly more than if either of the compounds were solely administered. In topical preparations the pharmaceutical carrier for topical applications constitutes a major amount of the preparation. Typically, the active ingredient is in a range of from about 0.01 to about 10 percent total weight of the topical composition, preferably 0.1 to 5 percent total weight.

Pharmaceutically acceptable salts of minoxidil or other vasodilators taught herein are for example acid addition salts which may be chosen from the following: acetate, adipate, alginate, aspartate, benzoate, benzenesulfonate, bisulfitte, butyrate, citrate, camphorate, camphorsulfonate, cyclopentanepropionate, digluconate, dodeclsulfate, ethanesultonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate.

Pharmaceutically acceptable cationic addition salts of minoxidil or other vasodilators include: pharmacologically acceptable metal cations, ammonium, amine cations, or quaternary ammonium cations. Especially preferred metal cations are those derived from the alkali metals, e.g., lithium, sodium, and potassium, and from the alkaline earth metals, magnesium and calcium, although cationic forms of other metals, e.g., aluminum, zinc, and iron are also within the scope of this invention. Pharmacologically acceptable amine cations are those derived from primary, secondary, and tertiary amines.

The composition of the invention may be administered topically in a water-base cream, ointment, or gel form. Several factors contribute to cosmetic advantages of the water-base composition. High drug loading up to 5% or more in non-crystalline form is possible, and the drug remains in a non-crystalline form up to several hours or more after administration, since solvent evaporation is relatively slow and evaporation can occur without leading to drug crystallization. Since the composition contains little or no alcohol, it can be applied without stinging.

The drug is efficiently taken up by the skin, by virtue of the selected amphipath, and different rates of uptake can be achieved by varying the drug or amphipath concentration, and by selection of different amphipathic compounds.

The water-base composition may additionally contain liposome or lipid-emulsion particles in which the drug can be entrapped in non-crystalline form. See U.S. Pat. Nos. 4,485,054 and 4,761,288 for teachings on methods of encapsulating minoxidil in multilamellar lipid vesicles to aid in drug delivery. In one embodiment, a concentrated liposomal composition having desired cream or ointment consistency can be formulated using a novel solvent injection system. The liposome formulation can have high loading, and a rate of drug uptake can be modulated by choice of lipid components and relative molar amounts of lipid and drug. The lipid formulation is also expected to have the known moisturizing benefits of topical lipid formulations. In addition or alternatively, liposomes are loaded with saw palmetto extract and/or nettle root extract.

In another embodiment, the composition is dispersed as an aerosol form, such as in a chlorofluorocarbon solvent, for delivery in spray form. The spray form has many advantages of the water-base formulation, including high drug loading and enhanced drug uptake. Additionally, the spray composition has the advantage that it can be applied in a more convenient manner and without matting the hair in the treated scalp region.

Other suitable additives/carriers that may be admixed with the minoxidil composition include, but are not limited to, water, glycols, esters, glycerine, alcohols, lipid materials, coloring agents, fragrances, anti-oxidants, thickening agents, ultra-violet light stabilizers, preservatives, and other pharmaceutically accepted additives.

The selection of additives may impact on the effectiveness of the composition. A particularly preferred safe and effective composition is based on a cosmetic carrier wherein a solvent system is an aqueous alcoholic solution containing ethanol, propanol or isopropanol, together with a lower alkyl($C_{1-C_4}$)glycol, such as ethylene glycol or propylene glycol and, usually, a thickener or gelling agent. Another, often useful additive is dimethicone or other volatile silicone solvent and carrier.

In a specific embodiment, the subject hair growth compositions can be provided in shampoo and/or conditioner form, which can preferably be used on a daily basis. The subject compositions can be added to shampoo formulations commonly used in the art and readily produce by one skilled in the art. In a preferred embodiment, mixtures of fatty acid esters of sorbitol and sorbitol anhydrides (commonly called polysorbates) are added to the shampoo formulations. These compounds have nonionic properties that inhibit shedding of hair. Polysorbates are one of a group of nonionic surfactants obtained by esterifcation of sorbitol with one or three molecules of a fatty acid (e.g. stearic, lauric, oleic, palmitic) under conditions which cause splitting out of water from the sorbitol, leaving sorbitan. In an even more preferred embodiment ethylene oxide is added along with the fatty acid esters in the condensation reaction to effect water solution.

In an alternative embodiment, the components of the subject hair growth composition can be administered orally as a safe dietary supplement. Preferably, the dietary supplement is taken concurrent to administration of the topical compositions described herein.

The subject hair growth stimulating compositions can be packaged in a kit with instructions for use and applicators commonly used in the art. The subject compositions can be contained in various bottles having engaged thereto spray nozzles for administrating the composition to the affected area.

The teachings of all patents and publications cited throughout this specification are incorporated by reference in their entirety to the extent not inconsistent with the teachings herein.

Following are examples which illustrate procedures for practicing the invention. These examples should not be construed as limiting. All percentages are by weight and all solvent mixture proportions are by volume unless otherwise noted. Where percentages do not amount to 100 percent, DI water is added to the formulation to meet the remaining percentages.

EXAMPLE 1

Hair Growth Stimulating Formulation for Topical Administration

| | |
|---|---|
| pharmaceutically-acceptable carrier | 35% to 99% |
| Minoxidil | 1% to 5% |
| Extract of Nettle Root | 1% to 3% |
| Saw Palmetto Extract | 3% to 8% |

EXAMPLE 2

Hair Growth Stimulating Formulation for Topical Administration

| | |
|---|---|
| pharmaceutically-acceptable carrier | 35% to 99% |
| Minoxidil | 1% to 5% |
| Dimethyl Isosorbide | 1% to 6% |
| Capsaicin | 0.5% to 2.5% |
| Niacin | 0.5% to 1.5% |
| Ginkgo Biloba | 1% to 3% |
| Extract of Nettle Root | 1% to 3% |
| Horsetail Extract | 2% to 4% |
| Saw Palmetto Extract | 3% to 8% |
| Peppermint Oil | 1% to 9% |
| Milk Thistle | 2% to 8% |
| Methyl Nicotinate | 0.5% to 4% |

EXAMPLE 3

Hair Growth Stimulating Formulation for Topical Administration

| | |
|---|---|
| Aloe Vera Gel | 35% to 99% |
| Minoxidil | 1% to 5% |
| Dimethyl Isosorbide | 1% to 6% |
| Rosemary Extract | 2% to 8% |
| Glycolic Acid | 2% to 6% |
| Pantothenic Acid | 1% to 3% |
| Glycerine | 10% to 12% |
| Safflower Oil | 8% to 16% |
| Capsaicin | 0.5% to 2.5% |
| Niacin | 0.5% to 1.5% |
| Ginkgo Biloba | 1% to 3% |
| Extract of Nettle Root | 1% to 3% |
| Horsetail Extract | 2% to 4% |
| Saw Palmetto Extract | 3% to 8% |
| Peppermint Oil | 1% to 9% |
| Milk Thistle | 2% to 8% |
| Methyl Nicotinate | 0.5% to 4% |

EXAMPLE 4

Hair Growth Stimulating Formulation for Topical Administration

| | |
|---|---|
| Aloe Vera Gel | 35% to 99% |
| Minoxidil | 1% to 5% |
| Dimethyl Isosorbide | 1% to 6% |
| Rosemary Extract | 2% to 8% |
| Glycolic Acid | 2% to 6% |
| Pantothenic Acid | 1% to 3% |
| Glycerine | 10% to 12% |
| Safflower Oil | 8% to 16% |
| Capsaicin | 0.5% to 2.5% |
| Niacin | 0.5% to 1.5% |
| Ginkgo Biloba | 1% to 3% |
| Extract of Nettle Root | 1% to 3% |
| Horsetail Extract | 2% to 4% |
| Saw Palmetto Extract | 3% to 8% |
| Peppermint Oil | 1% to 9% |
| Milk Thistle | 2% to 8% |
| Methyl Nicotinate | 0.5% to 4% |
| Phospholipid | 2% to 8% |

EXAMPLE 5

Hair Growth Stimulating Formulation for Topical Administration

| | |
|---|---|
| Aloe Vera Gel | 35% to 99% |
| Minoxidil | 1% to 5% |
| Capsaicin | 0.5% to 2.5% |
| Niacin | 0.5% to 1.5% |
| Ginkgo Biloba | 1% to 3% |
| Extract of Nettle Root | 1% to 3% |
| Saw Palmetto Extract | 3% to 8% |
| Peppermint Oil | 1% to 9% |
| Milk Thistle | 2% to 8% |
| Methyl Nicotinate | 0.5% to 4% |
| Phospholipid | 2% to 8% |

EXAMPLE 6

Hair Growth Stimulating Formulation for Topical Administration

| | |
|---|---|
| pharmaceutically-acceptable carrier | 35% to 99% |
| Minoxidil | 1% to 5% |
| Extract of Nettle Root | 1% to 3% |
| Saw Palmetto Extract | 3% to 8% |
| phospholipid | 2% to 8% |

EXAMPLE 7

Hair Growth Stimulating Formulation for Topical Administration

| | |
|---|---|
| pharmaceutically-acceptable carrier | 35% to 99% |
| Minoxidil | 1% to 5% |
| Extract of Nettle Root | 1% to 3% |
| Saw Palmetto Extract | 3% to 8% |
| Phospholipid | 2% to 8% |
| Niacin | 0.5% to 1.5% |
| Capsaicin | 0.5% to 2.5% |

EXAMPLE 8

Formulation for Dietary Supplement for Consumption in Conjunction with Topical Formulation

| | |
|---|---|
| Niacin | 30 mg |
| Vitamin $B_6$ | 25 mg |
| Folate | 200 mcg |
| Biotin | 130 mcg |
| Panthothenic acid | 30 mg |
| Iodine | 150 mcg |
| Zinc | 15 mg |
| pumpkin seed concentrate | 60 mg |
| Ginkgo Biloba | 30 mg |
| Fo ti root | 100 mg |
| L-Histidine | 50 mg |
| Aloe vera gel | 20 mg |
| Gotu Kola leaf | 30 mg |
| Saw Palmetto berry | 200 mg |
| Nettle leaf | 180 mg |
| Sage leaf | 20 mg |
| Hawthorn berry | 60 mg |
| Bovine extract | 30 mg |
| Sulfur | 20 mg |
| Silica | 25 mg |

The above formulation is preferably put in tablet form. Preferably two tablets are taken twice a day concurrent with administration of topical formulations described in Examples 1–7 and elsewhere herein.

EXAMPLE 9

Topical Formulation

| Aloe Vera Gel | 35% to 99% |
|---|---|
| Minoxidil | 3% to 5% |
| Rosemary Extract | 0.5% to 1% |
| Glycolic Acid | 0.2% to 1% |
| Tween | 1% to 3% |
| Glycerine-USP | 5% to 7% |
| Isopropyl alcohol | 9% to 11% |
| Capsaicin | 1% to 2.5% |
| Arlasolve DMI | 0.6% to 1% |
| Niacin | 0.5% to 1.5% |
| glycerol oxide esters | 1% to 2% |
| Ginkgo Biloba | 1% to 3% |
| Extract of Nettle Root | 1% to 3% |
| Horsetail Extract | 1% to 2% |
| Peppermint Oil | 0.2% to 1% |
| Milk Thistle | 1% to 2% |
| Glydant Plus | 0.2% |
| Methyl Nicotinate | 0.05% to 1% |

EXAMPLE 10

Clinical Study

Participants consisted of five males between the ages of 18 and 40, who were all experiencing hair loss of various degrees. The participants applied the formulation described in Example 9 to their scalps once daily, and ingested two tablets described in Example 8 twice daily. The scalps of the participants were evaluated every four weeks. Clinic follow up visits consisted of photographs, progress questionnaires completed by the participant, and study drug compliance. The results with respect to the amount of hair loss or initiation of new hair growth is noted below:

Two months—participants report slowing of hair loss and the beginning signs of new hair growth.

Three months—participants report no noticeable hair loss and new hair growth. Reports of new, "downy" type hair where topical solution has been applied were given.

Four months—participants report that hair is slowly getting thicker, and stronger.

Five months—participants fuller hair and definite reduction of hair loss.

Comments of hair growth with respect to location was dependent on the individual, location of each participant's hair loss, and where the topical solution was applied. Some participants reported hair growth in the apex area, as well as growth in the frontal region of the scalp.

It should be understood that the examples and embodiments described herein are for illustrative purposes only and that various modifications or changes in light thereof will be suggested to persons skilled in the art and are to be included within the spirit and purview of this application and the scope of the appended claims.

Reference

Brodland and Muller (1991) *Cutis* 47:173–176.

Katzx, H. I. (198) *Clin. Dermatol.*, 6:196–199.

Puolakka, J. (1980) *Acta. Obset. Gynecol. Scand., suppl.* 95:35–41.

Rushton, D. H., D. D. Ramsay (1992) "The importance of adequate serum ferritin levels in cyproterone acetate and ethinyl-oestradiol therapy in women with diffuse androgen-dependent alopecia," *Clin. Edocrinal.* 36:421–427.

Ruston D. H., W. Futterwiet, D. H. Kingsley,P. Kingsley and M. J. Norris (1991) "Quantative assessment of spironolactone treatment in women with diffuse androgen-dependent alopecia," *J. Soc. Cosmet. Shem.* 42:317–325.

Zapacosta, A. R. (1980) *N. Eng. J. Med.* 303:1480–1481.

U.S. Pat. No. 3,551,554.
U.S. Pat. No. 3,989,816.
U.S. Pat. No. 4,017,641.
U.S. Pat. No. 4,132,781.
U.S. Pat. No. 4,139,619.
U.S. Pat. No. 4,485,054.
U.S. Pat. No. 4,596,812.
U.S. Pat. No. 4,761,288.
U.S. Pat. No. 4,861,764.
U.S. Pat. No. 5,030,442.
U.S. Pat. No. 5,620,980.
PCT Application No. WO 92/16236.

What is claimed is:

1. A dietary supplement comprising minoxidil, saw palmetto extract, and nettle root extract.

2. The dietary supplement of claim 1 further comprising one or more of the following components:
   (a) niacin;
   (b) vitamin B6;
   (c) folate;
   (d) biotin;
   (e) panthothenic acid;
   (f) iodine;
   (g) zinc;
   (h) pumpkin seed concentrate;
   (i) Ginkgo biloba;
   (j) fo ti root;
   (k) L-histidine;
   (l) aloe vera gel;
   (m) gotu kola leaf;
   (n) sage leaf;
   (o) Hawthorne berry;
   (p) bovine extract;
   (q) sulfur; or
   (r) silica.

3. A topical composition for application to the scalp, said composition comprising a admixture of minoxidil, saw palmetto extract, and nettle root extract.

4. A topical composition for application to the scalp, said composition comprising, in admixture of pharmaceutically acceptable carrier, minoxidil, and saw palmetto extract and one or more of the following:
   a.) Nettle root extract;
   b.) Capsaicin;
   c.) Niacin;
   d.) Gingko Biloba;
   e.) horsetail extract;
   f.) phospholipid;
   g.) glycerol oxide esters;
   h.) cyclodextrin;
   i.) ketoconazole;
   j.) urosolic acid
   k.) polysorbate;
   l.) 1,4,3,6 dianhydro-2,5-di-o-methyl-D-glucitol;
   m.) peppermint oil
   n.) silica
   o.) milk thistle; or
   p.) methyl nicotinate.

5. The topical composition of claim 4, wherein minoxidil comprises about 1 percent to about 5 percent, by weight, of said composition.

6. The topical composition of claim 4, wherein said pharmaceutically acceptable carrier is water, glycols, esters, alcohols, lipids, or combinations thereof.

7. The topical composition of claim 6, wherein said pharmaceutically acceptable carrier is a mixture of isopropyl alcohol and glycerine.

8. A kit for stimulating hair growth comprising a container having the composition of claim 4 disposed therein and instructions for use.

9. A topical composition for application to the scalp, said composition comprises a pharmaceutically acceptable carrier, minoxidil, saw palmetto extract, nettle root extract and phospholipid.

10. The topical composition of claim 9, wherein minoxidil comprises about 1 percent to about 5 percent, nettle root extract comprises about 1 percent to about 3 percent and phospholipid comprises about 2 percent to about 8 percent, by weight, of said composition.

11. A topical composition for application to the scalp, said composition comprises a pharmaceutically acceptable carrier, minoxidil, saw palmetto extract, nettle root extract, capsaicin, niacin, and horsetail extract.

12. The topical composition of claim 11, wherein minoxidil comprises about 1 percent to about 5 percent, nettle root extract comprises about 1 percent to about 3 percent, capsaicin comprises about 0.5 percent to about 2.5 percent, niacin comprises about 0.5 percent to about 2.0 percent and horsetail extract comprises about 2 percent to about 4 percent, by weight, of said composition.

13. The topical composition of claim 11 further comprising methyl nicotinate.

14. The topical composition of claim 13, further comprising phospholipid.

15. A method of stimulating hair growth in a patient comprising obtaining a composition according to claim 11, and administering said composition to said patient's scalp.

16. The method of claim 15, further comprising co-administering, orally, a dietary supplement comprising minoxidil, saw palmetto extract, and nettle root extract, wherein co-administering occurs prior to, concurrently, or subsequent to said administering of said topical composition.

* * * * *